United States Patent
Van Der Schaaf et al.

(10) Patent No.: US 9,592,954 B2
(45) Date of Patent: Mar. 14, 2017

(54) PACKAGE COMPRISING FEEDING MATERIALS FOR CUT FLOWERS

(75) Inventors: Tjerk Pier Van Der Schaaf, Lelystad (NL); Ewald Groenewoud, Huizen (NL); Paul Thomas Dirk Herman, Swifterbant (NL)

(73) Assignee: Chrysal International BV, Naarden (NL)

( * ) Notice: Subject to any disclaimer, the term of this patent is extended or adjusted under 35 U.S.C. 154(b) by 1597 days.

(21) Appl. No.: 11/756,784

(22) Filed: Jun. 1, 2007

(65) Prior Publication Data

US 2007/0267317 A1 Nov. 22, 2007

Related U.S. Application Data

(62) Division of application No. 10/311,244, filed as application No. PCT/NL01/00446 on Jun. 13, 2001, now abandoned.

(30) Foreign Application Priority Data

Jun. 13, 2000 (NL) ...................................... 1015423

(51) Int. Cl.
| | |
|---|---|
| *A01G 5/06* | (2006.01) |
| *A47G 7/06* | (2006.01) |
| *B65D 85/808* | (2006.01) |
| *A01N 3/02* | (2006.01) |

(52) U.S. Cl.
CPC ............. *B65D 85/808* (2013.01); *A01G 5/06* (2013.01); *A01N 3/02* (2013.01); *A47G 7/06* (2013.01)

(58) Field of Classification Search
USPC ...... 47/41.01, 41.13, 48.5, 59 R, 62 E, 62 R, 47/65, 65.8, 79, 80, 58.1 R, 58.1 CF
See application file for complete search history.

(56) References Cited

U.S. PATENT DOCUMENTS

| | | | |
|---|---|---|---|
| 3,874,871 A | 4/1975 | Sy et al. | |
| 4,167,832 A | 9/1979 | Zetterquist et al. | |
| 5,022,182 A | 6/1991 | Anderson | |
| 5,112,380 A | 5/1992 | Yamamoto et al. | |
| 5,698,004 A * | 12/1997 | Hartmann | ........................ 71/55 |
| 5,942,021 A | 8/1999 | Stirrup | |

(Continued)

FOREIGN PATENT DOCUMENTS

| | | | |
|---|---|---|---|
| EP | 0405944 | * | 1/1991 |
| EP | 0 649 796 A1 | | 4/1995 |

(Continued)

*Primary Examiner* — David Parsley
(74) *Attorney, Agent, or Firm* — Leydig, Voit & Mayer, Ltd.

(57) ABSTRACT

A sachet assembly, includes a closed bag which is formed from water-permeable filter paper, and a solid substance which is contained in the bag and is at least partially water-soluble. The water-soluble solid substance comprises a preparation for cut flowers. In particular, the preparation comprises a foodstuff and/or conditioning agent and/or disinfectant and/or biocide and/or growth inhibitor. The packaging assembly includes a waterproof, or at least moisture-proof, outer packaging containing a large number of sachets. The invention also relates to the use of a sachet made from water-permeable filter paper for administering a preparation to cut flowers which are standing in water.

11 Claims, 3 Drawing Sheets

(56) References Cited

U.S. PATENT DOCUMENTS

| | | | |
|---|---|---|---|
| 5,974,730 A | 11/1999 | Chien | |
| 6,083,535 A | 7/2000 | Chiba et al. | |
| 6,133,237 A | 10/2000 | Noll et al. | |
| 6,289,630 B1 | 9/2001 | Hetze et al. | |
| 6,484,442 B1 | 11/2002 | Weder | |
| 6,505,425 B1 | 1/2003 | Gilbert | |
| 6,606,821 B1 * | 8/2003 | Connelly | 47/48.5 |
| 6,735,902 B1 | 5/2004 | Ahm | |
| 2006/0073972 A1 | 4/2006 | Plus | |

FOREIGN PATENT DOCUMENTS

| | | |
|---|---|---|
| FR | 822 483 | 12/1937 |
| FR | 2611669 * | 9/1988 |
| JP | 1156055 | 6/1989 |
| JP | 10127192 | 5/1998 |
| JP | 2000-143101 A | 5/2000 |
| WO | WO 98/42180 | 10/1998 |

* cited by examiner

PUT THE SACHET WITHOUT OPENING IN 2 LITERS OF WATER

PACKAGE COMPRISING FEEDING MATERIALS FOR CUT FLOWERS

CROSS-REFERENCE TO RELATED APPLICATION

This patent application is a divisional of copending U.S. patent application Ser. No. 10/311,344, filed Aug. 18, 2003.

FIELD OF THE INVENTION

The present invention relates to a sachet, in particular a sachet assembly, comprising:
a closed bag which is formed from water-permeable filter paper and
a solid substance which is contained in the bag and is at least partially water-soluble.

BACKGROUND OF THE INVENTION

A sachet assembly including alternate contents is known. One could think, for example, of a tea bag, which is formed from a filter paper, also known as tea bag paper, in which, a certain quantity of optionally comminuted tea leaves is packaged. A tea bag of this type is, as is known, generally provided with a string which can be used to hang it in a tea cup or tea pot so that, once the tea has brewed sufficiently, the string can be used to remove it again from the cup or teapot.

OBJECTS OF THE INVENTION

It is an object of the present invention to provide a preparation for cut flowers in an administration form which is such that it is ensured and can be checked that a specific dose has been administered to the water in which the cut flowers are standing.

SUMMARY OF THE INVENTION

According to the invention, this object is achieved by the fact that, in the sachet of the type described in the introduction, the water-soluble solid substance comprises a preparation for cut flowers. A sachet of this type can be placed in the water in a container holding cut flowers which are standing in water, after which the water can enter the bag via the filter paper, so that the preparation is dissolved, and then carries the preparation, out of the bag in dissolved form. Since the bag is closed, administration of one bag ensures that a specific dose is administered. Furthermore, the bag will remain present even after it has been administered to the water, which makes it easy to check that the preparation has been administered. Therefore, it is possible for both the purchaser, such as a florist or consumer, to see that the cut flowers which have been purchased are in water which has been appropriately treated, and also it is possible for an inspection body to establish, in a simple and efficient way, that a specific dose has been administered to cut flowers. An inspection body of this type may, for example, be a body which checks the quality of goods on behalf of a professional association of cut-flower traders, but may also, for example, be a supplier or purchaser of cut flowers who wishes to check whether the cut flowers which he has supplied are treated correctly.

Advantageously, the preparation in the sachet according to the invention will comprise a food and/or conditioning agent and/or disinfectant and/or biocide and/or growth inhibitor. In this context, the term conditioning agent is understood in particular as meaning an agent which is used to adjust the state of the water, such, as its hardness or pH. The term growth inhibitor is understood as meaning an agent which inhibits the growth, of microorganisms, so that the water uptake and food uptake by the cut flowers remains appropriate.

Furthermore, in the sachet according to the invention, it is advantageous if the filter paper is semi-permeable. In this context, the term semi-permeable is understood as meaning, in particular, permeability to particles up to a maximum size of 100 to 400 µm.

With a view to ease of production, it is advantageous, in the sachet according to the invention, if the bag is rectangular in shape. In connection with the final administration of a sachet of this type to a container, such as a bucket, holding a quantity of water of the order of magnitude of 1 to 5 liters, although sometimes more liters, it is in this case preferable if the rectangular bag has dimensions of 2 to 8 cm wide by 2 to 12 cm long.

Furthermore, in a sachet according to the invention, it is advantageous if the bag is provided on the outside with an image, in particular, obtained using a printing technique. Filter paper is eminently suitable for an image to be applied thereto, for example, with the aid of a printing technique such as a flexographic printing technique. The image may in this case be applied to the filter paper before the filter paper is formed into a bag. In this way, it is possible to provide the bag with an advertising message. In particular, however, it is advantageous for the bag in this way to be provided with instructions for use or application. However, it is also highly useful and advantageous for the bag to be provided with an indication of the preparation contained therein in this way. Such an indication may, for example, be a brand name, but may also be a list of the ingredients or active constituents. It is also possible to provide the bag with warnings in this way.

Furthermore, in the sachet according to the invention, it is advantageous if the bag is made from a filter material which, when it takes up water, becomes transparent or translucent, in such a manner that the contents become visible. In this way, it is possible to check, when the bag has been put in water, that the contents are present in the bag. In this case, it is also advantageous if the entire contents are water-soluble. This is because in this way it is possible, by visual inspection, to determine whether the sachet is still active. This also makes it possible to prevent errors, since it can be determined visually whether an empty or used bag/sachet assembly has been added to the cut flowers. For this purpose, it is also possible to use an ink which changes color when the active substances have been exhausted. In this regard, consideration may be given, for example, to pH indicators, such as litmus.

Furthermore, in the sachet according to the invention, it may be advantageous if the water-soluble material is hygroscopic.

The invention also relates to a packaging assembly comprising a waterproof, or at least moisture-proof, outer packaging containing a large number of sachets according to the invention. A packaging assembly of this type can be used to ensure that the sachets arrive at the user in good condition and, moreover, can be stored in good condition for a certain time by the user. The outer packaging will in this case preferably be a waterproof or at least moisture-proof recloseable outer packaging. Consideration may be given, for example, to a plastic bucket with a lid which can seal onto the upper rim of the bucket via a, preferably clamping, labyrinth seal.

The invention also relates to the use of a sachet made from water-permeable filter paper for administering a preparation, such as a food, and/or conditioning agent and/or disinfectant and/or biocide and/or growth inhibitor for microorganisms, to cut flowers which are standing in water.

BRIEF DESCRIPTION THE DRAWING(S)

In the text which follows, the present invention will be explained in more detail with reference to examples which are illustrated in the drawings, in which.

DETAILED DESCRIPTION OF THE INVENTION

Figure 1:
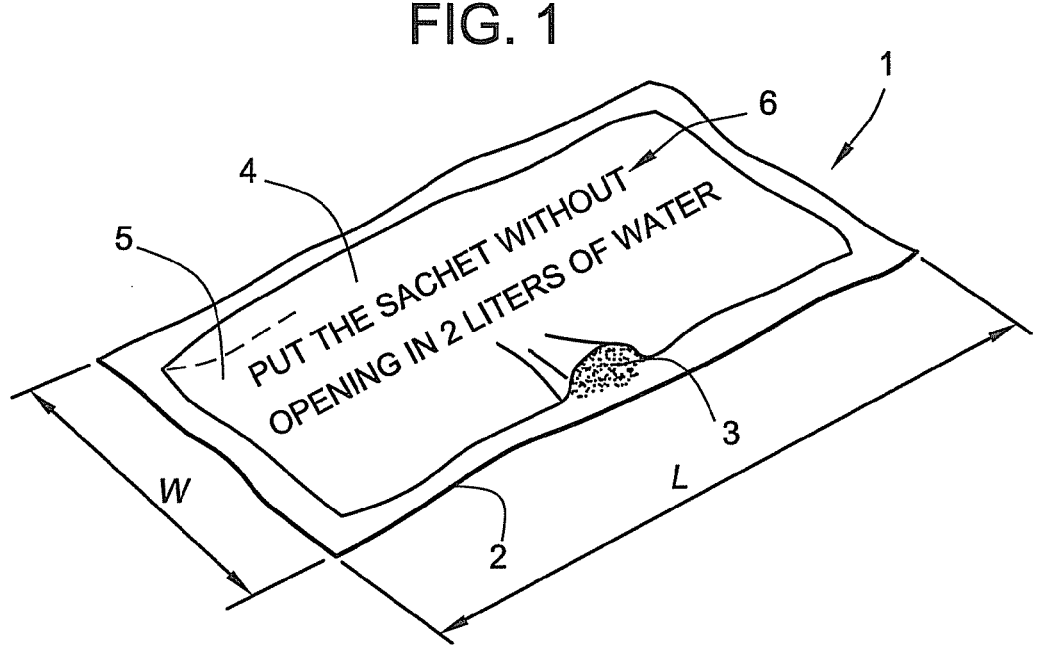
FIG. 1 shows a diagrammatic and perspective, partially cut-away view of a sachet assembly according to the invention.

FIG. 1 shows a sachet according to the invention. The sachet 1 according to the invention, comprises a bag 2 comprising water-permeable filter paper. The bag 2 is composed of a rectangular upper panel 4 and a rectangular lower panel 5, which panels are joined together along their periphery, for example by an adhesive bond. A preparation 3, which is partially shown in a cut-away section, is situated in the bag 2. This preparation 3 contains in particular, a food and/or a disinfectant and/or a biocide. The preparation 3 may be a powder or granules, but may also be a solid substance in some other form. The preparation 3 may be entirely water-soluble, but may also be partially water-soluble. In particular, it is conceivable for the preparation 3 to comprise a substrate which is not water-soluble, in which substrate the soluble preparation is situated. Then, when the substrate comes into contact with water, the preparation will be dissolved and will be released from the substrate.

As shown in FIG. 1 for the upper panel 4, the bag 2 may be printed. In the example illustrated, the printing represents instructions for use, namely put sachet without opening in 2 liters of water.

The length L of the sachet which is illustrated by way of example in FIG. 1 is approximately 9 cm, while its width W is approximately 5 cm. However, it should be clear that these dimensions, which are given by way of example for the length L and width W, are purely illustrative. These dimensions may vary within wide limits. By way of example, the dimension for the length L may vary in a range from 2 to 16 cm, although smaller or larger dimensions for the length L are also conceivable. The width dimension W may, for example, vary in a range from 2 to 10 cm, although in this case too, both smaller and larger width dimensions are conceivable.

It should be noted that, although FIG. 1 shows a rectangular sachet, the sachet may also be square, round, triangular or trapezium-shaped, or whatever other form may be desired.

Figure 2:
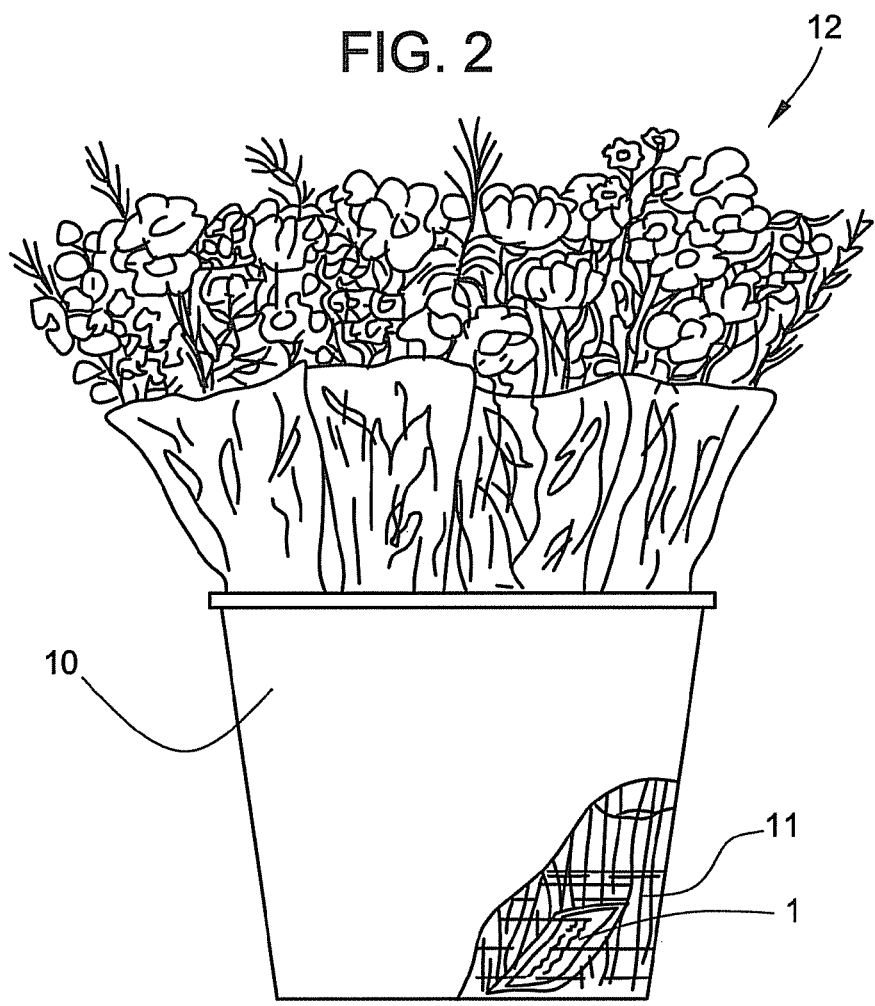
FIG. 2 shows a diagrammatic, side elevational, partially cut-away view of a bucket holding cut flowers, which contains a sachet assembly according to the invention.

FIG. 2 shows, by way of example, a bucket 10 containing cut flowers 12 standing in water 11. A sachet 1 according to the invention is situated in this bucket.

Figure 3:
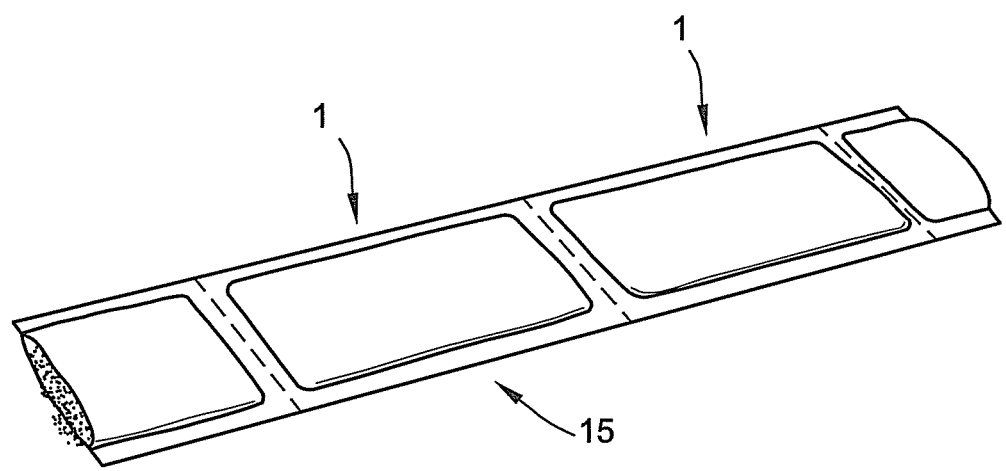
FIG. 3 shows a fragmentary perspective view of an exemplary strand of multiple sachets according to the disclosure.

FIG. 3 shows, by way of example, a strand 15 according to the invention comprising a multiplicity of sachets 1 according to the invention.

Figure 4:
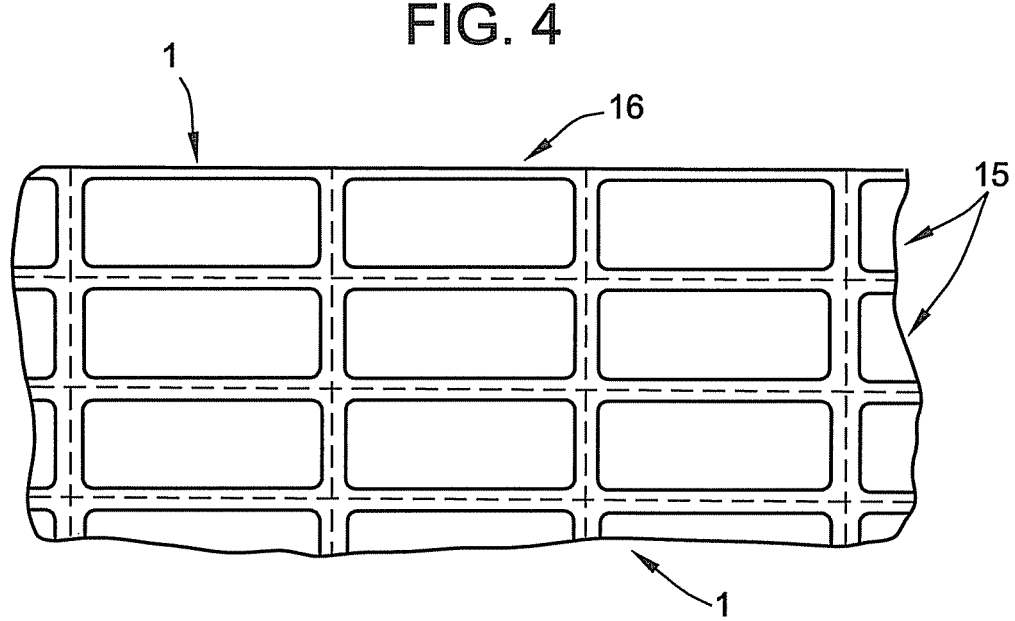
FIG. 4 shows a fragmentary plan view of an exemplary web of multiple sachets according to the disclosure.

FIG. 4 shows, by way of example, a web 16 according to the invention comprising a multiplicity of sachets 1 according to the invention. The web 16 can be considered as being composed of a number of parallel strands 15 as shown in FIG. 3 which are joined together at their sides. Providing the sachets according to the invention in web, sheet or strand form has the considerable advantage of increasing the ease of handling, in particular for automated processing, of the sachets considerably.

Figure 5:
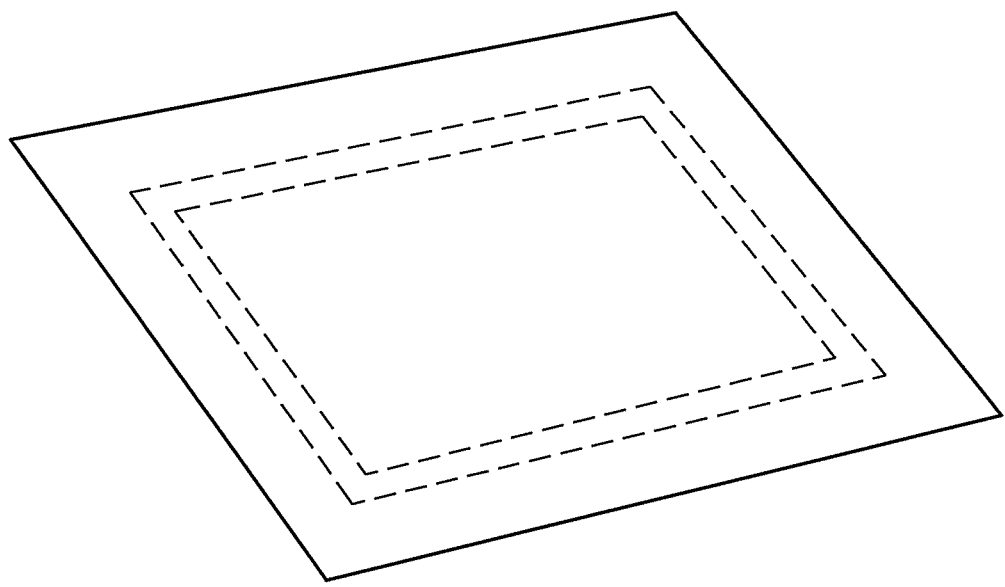
FIG. 5 shows a perspective view of an exemplary moisture-proof outer packaging for a sachet according to the disclosure.

FIG. 5 shows, by way of example, moisture-proof outer packaging for a sachet constructed according to teachings of the invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of providing a preparation to cut flowers, said method combining the steps of:

providing liquid water,
providing a sachet, said sachet comprising
- a closed bag which is formed from water-permeable material, and
- a solid substance is contained in the bag, said solid substance being water-soluble, the water-soluble solid substance being a preparation for cut flowers, providing a container adapted to hold and maintain liquid water, as opposed to allowing water to pass through the container,
combining said liquid water and said sachet in said container such that the water-permeable material becomes transparent or translucent when saturated with said liquid water such that said solid substance is visible and may be observed through the liquid water and the material, and
placing said cut flowers in said container in contact with said liquid water, said container containing said liquid water and said sachet.

2. The method according to claim 1 wherein said liquid water permeable material is a filter paper, and the method further comprises the step of observing said solid substance through the filter paper when said sachet is disposed in said liquid water and said filter paper is wet, whereby an observer observes whether said solid substance is present and whether said solid substance is dissolved, and thus whether the sachet should be replaced.

3. The method according to claim 1 wherein the preparation comprises at least one of the following: a food, conditioning agent, disinfectant, biocide, and/or growth inhibitor.

4. The method according to claim 2, in which the filter paper is semi-permeable.

5. The method according to claim 1, in which the bag has a rectangular shape.

6. The method according to claim 1, wherein the closed bag has an outside, and the bag is provided on the outside with a printed image.

7. The method according to claim 6, in which the image comprises instructions for use or application.

8. The method according to claim 1 wherein the step of providing a sachet comprises the steps of providing a plurality of sachets joined together to form a strand, and separating a sachet from said plurality.

9. The method according to claim 8 wherein the step of providing a plurality of sachets joined together to form a strand comprises the step of providing a plurality of parallel strands joined laterally to one another to form a sheet or web.

10. The method according to claim 1 wherein the step of providing a sachet comprises the step of providing a plurality of sachets, and the method further comprises the steps of providing a moisture-proof packaging containing said plurality of sachets, and removing a sachet from said moisture-proof packaging.

11. The method of according to claim 1 wherein the sachet maintains its integrity in liquid water for at least a period of time sufficient to allow the solid substance contained in the sachet to dissolve and pass through the water permeable material.

* * * * *